United States Patent
Weber et al.

(10) Patent No.: US 11,974,836 B2
(45) Date of Patent: May 7, 2024

(54) MULTI-PART APPLIANCE FOR NON-INVASIVE DETECTION OF VITAL PARAMETERS

(71) Applicant: PULSION MEDICAL SYSTEMS SE, Feldkirchen (DE)

(72) Inventors: Aaron Weber, Markt Schwaben (DE); André Hein, Esslingen am Neckar (DE)

(73) Assignee: PULSION MEDICAL SYSTEMS SE, Feldkirchen (DE)

( * ) Notice: Subject to any disclaimer, the term of this patent is extended or adjusted under 35 U.S.C. 154(b) by 520 days.

(21) Appl. No.: 17/272,247

(22) PCT Filed: Aug. 27, 2019

(86) PCT No.: PCT/EP2019/072848
§ 371 (c)(1),
(2) Date: Feb. 26, 2021

(87) PCT Pub. No.: WO2020/043726
PCT Pub. Date: Mar. 5, 2020

(65) Prior Publication Data
US 2021/0307633 A1 Oct. 7, 2021

(30) Foreign Application Priority Data
Aug. 29, 2018 (DE) ...................... 10 2018 006 846.4

(51) Int. Cl.
*A61B 5/022* (2006.01)
*A61B 5/0225* (2006.01)
*A61B 5/0235* (2006.01)

(52) U.S. Cl.
CPC ...... *A61B 5/02241* (2013.01); *A61B 5/02255* (2013.01); *A61B 5/0235* (2013.01)

(58) Field of Classification Search
None
See application file for complete search history.

(56) References Cited

U.S. PATENT DOCUMENTS

| 4,406,289 A | 9/1983 | Wesseling et al. |
| 4,524,777 A | 6/1985 | Kisioka et al. |

(Continued)

FOREIGN PATENT DOCUMENTS

| GB | 315409 A | * 3/1930 | ............. F16N 21/02 |
| GB | 1025633 A | 4/1966 | |

(Continued)

OTHER PUBLICATIONS

International Search Report for Application No. PCT/EP2019/072848 dated Nov. 18, 2019.

*Primary Examiner* — Benjamin S Melhus
*Assistant Examiner* — Samuel C Kim
(74) *Attorney, Agent, or Firm* — Patterson + Sheridan, LLP

(57) ABSTRACT

Disclosed herein is a base device with a pump device for applying pressure to a working fluid and a body contact device that can be detachably coupled to one another. A housing of the base device has a contact surface for the body contact device where the contact surface has a passage which can be closed by means of a closing member of a valve device. A spring is provided for applying spring force to move the closing member into a position that closes the passage. The body contact device has a pressure applicator, which can be acted upon by the working fluid, to apply pressure to the finger and a sealing element for creating a fluid connection with the base device. The body contact device has a deflecting means for deflecting the closing member against the spring force in the operating configuration.

13 Claims, 6 Drawing Sheets

(56) References Cited

U.S. PATENT DOCUMENTS

Figure 6:
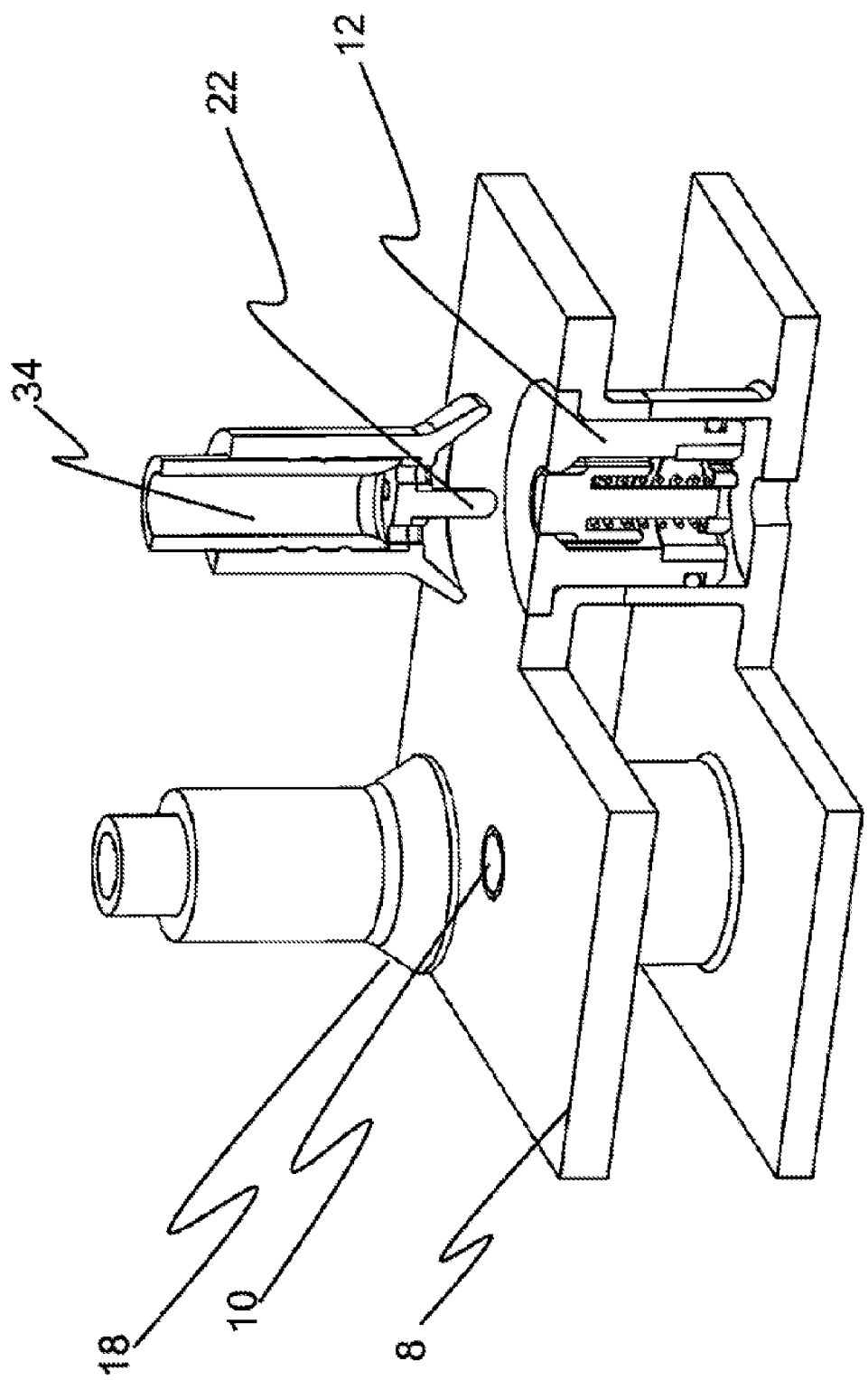

| | | |
|---|---|---|
| 4,726,382 A | 2/1988 | Boehmer et al. |
| 5,735,798 A | 4/1998 | Shinohara et al. |
| 6,669,648 B1 | 12/2003 | Fortin et al. |
| 2006/0195034 A1 | 8/2006 | Skrabal et al. |
| 2007/0032729 A1 | 2/2007 | Fortin |
| 2015/0038859 A1 | 2/2015 | Dalvi et al. |
| 2018/0045312 A1* | 2/2018 | Rosenberger .......... F16J 15/025 |
| 2018/0235478 A1 | 8/2018 | Khachaturian et al. |
| 2019/0150765 A1 | 5/2019 | Fortin et al. |

FOREIGN PATENT DOCUMENTS

| | | |
|---|---|---|
| WO | 2000059369 A2 | 10/2000 |
| WO | 2004086963 A2 | 10/2004 |
| WO | 2005037097 A1 | 4/2005 |
| WO | 2010050798 A1 | 5/2010 |
| WO | 2011045138 A1 | 4/2011 |
| WO | 2011051819 A1 | 5/2011 |
| WO | 2011051822 A1 | 5/2011 |
| WO | 2012032413 A2 | 3/2012 |
| WO | 2017143366 A1 | 8/2017 |
| WO | 20200043726 A1 | 3/2020 |

\* cited by examiner

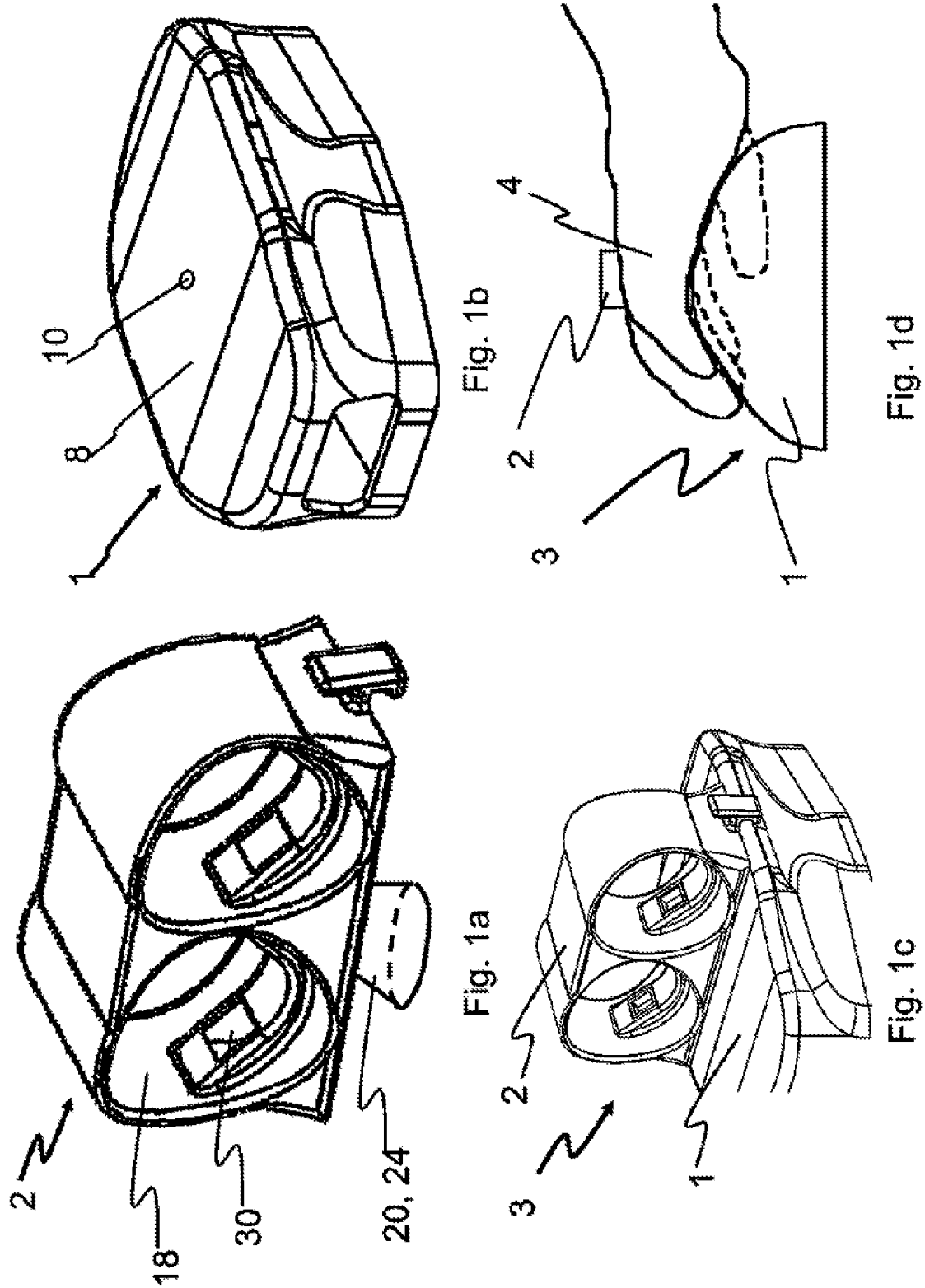

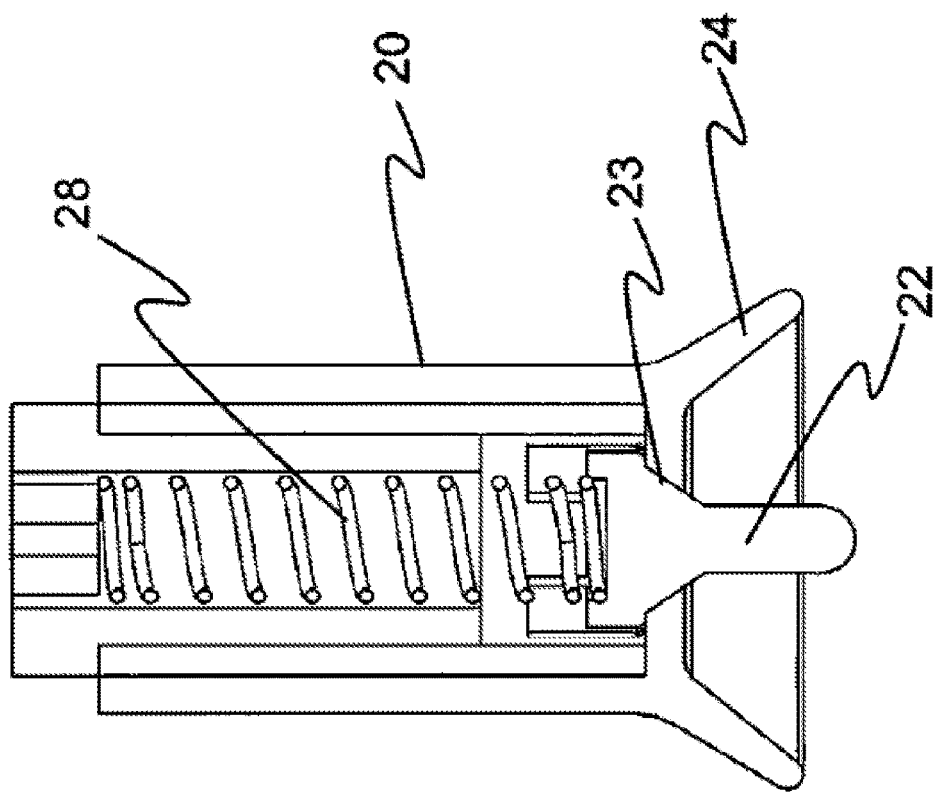
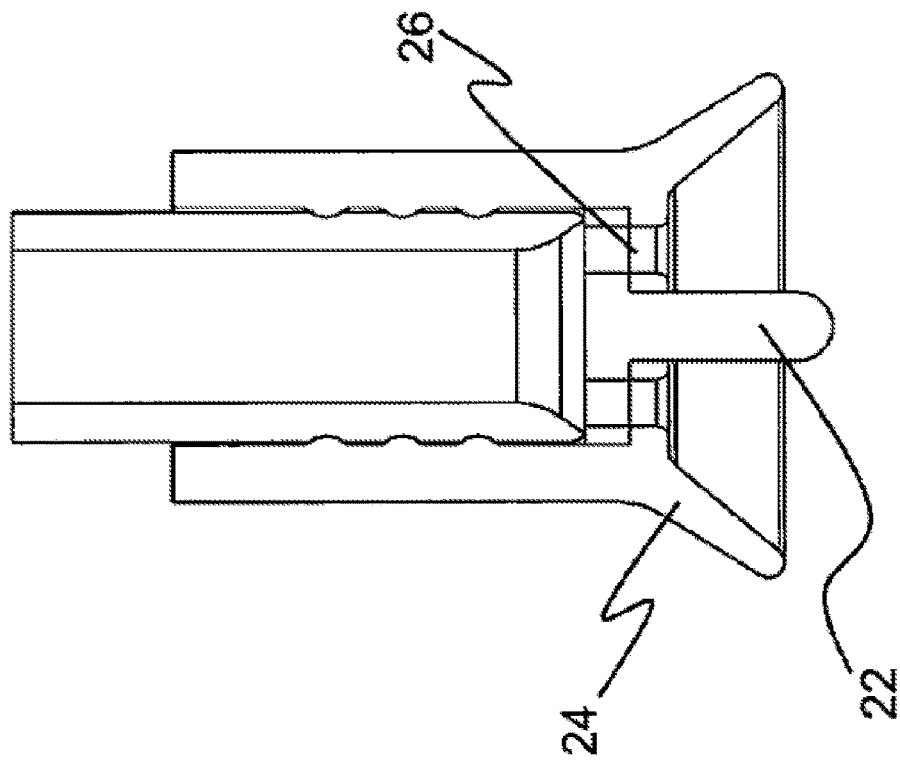
Fig. 2a
Fig. 2b

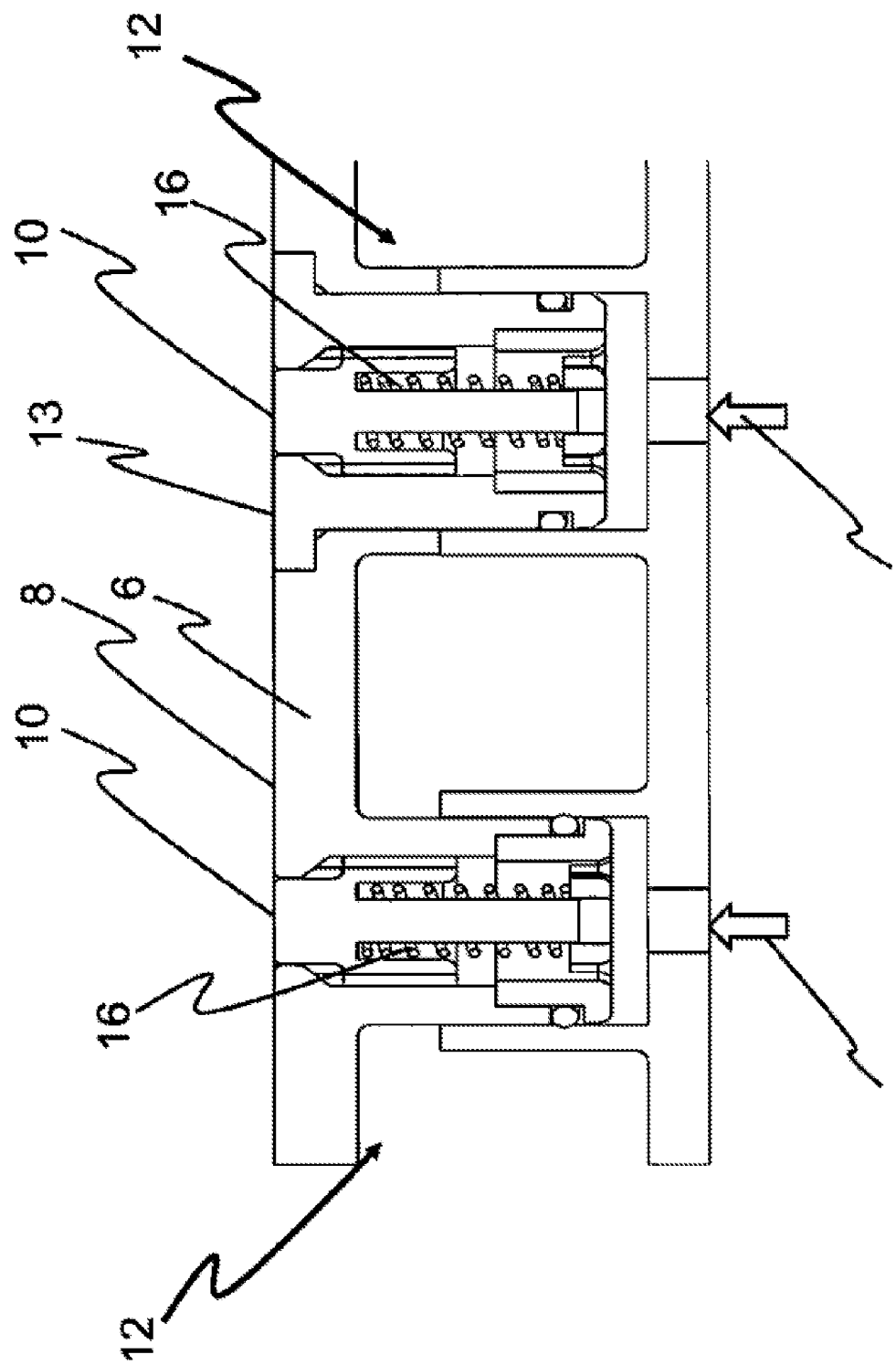

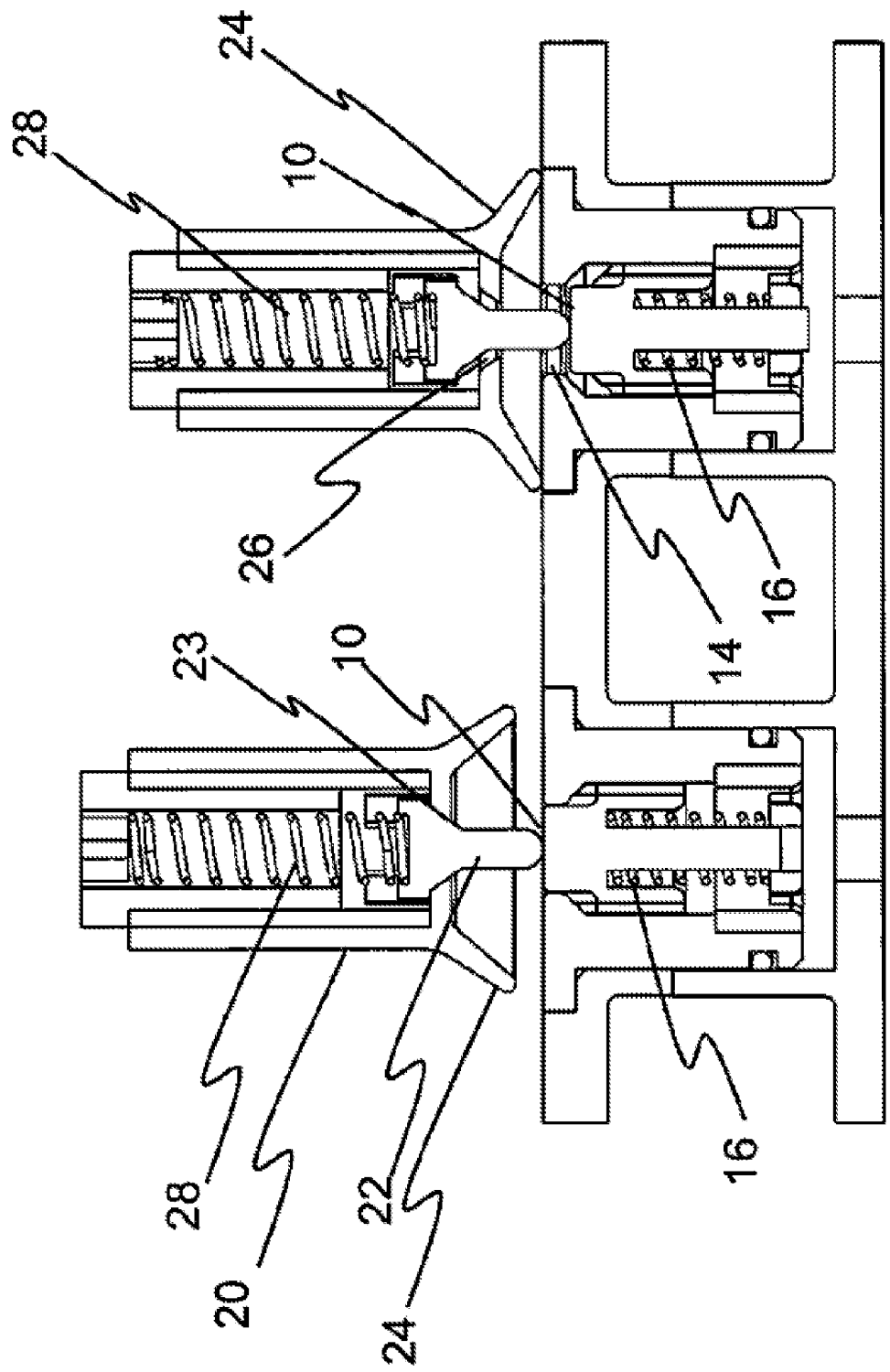

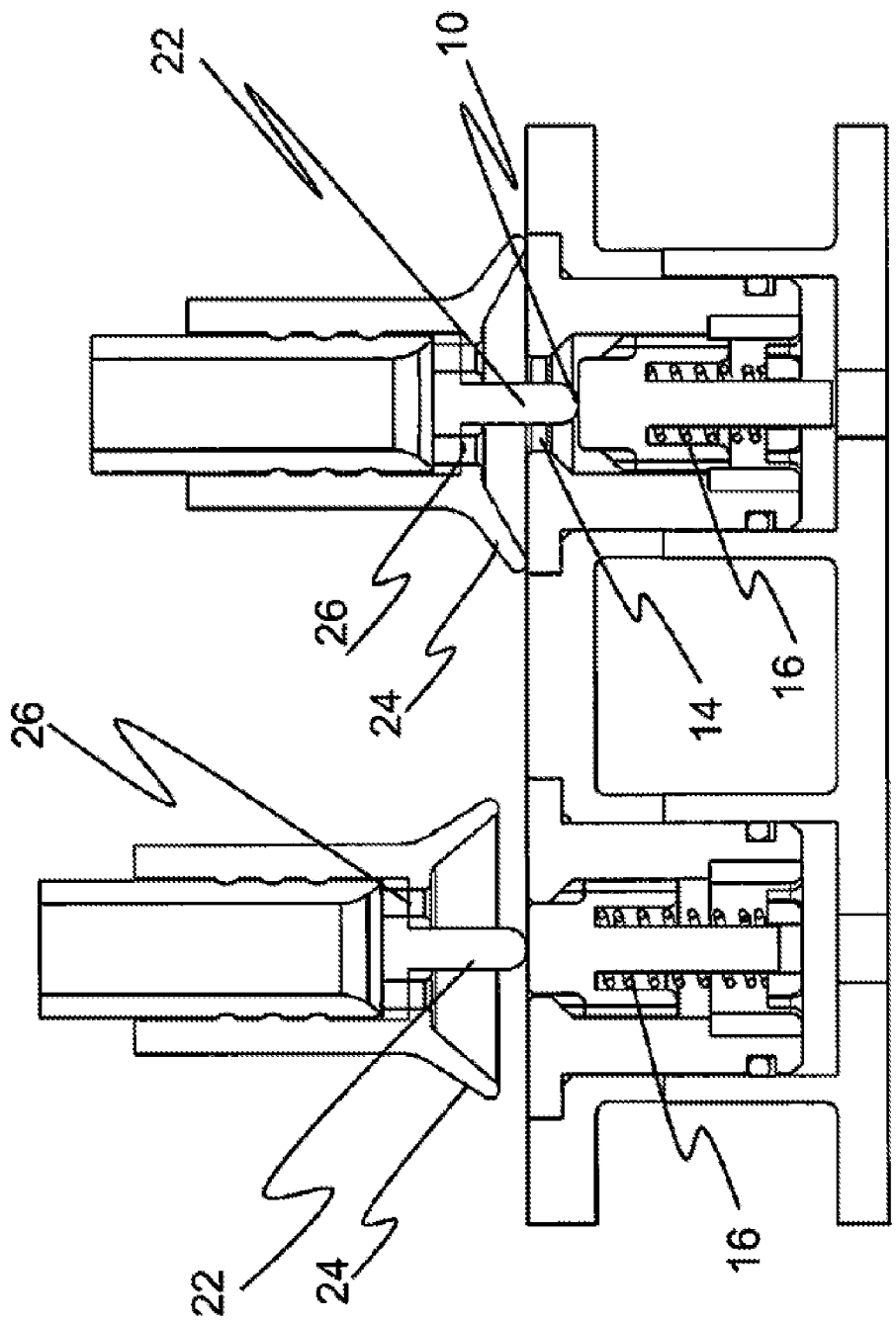

MULTI-PART APPLIANCE FOR NON-INVASIVE DETECTION OF VITAL PARAMETERS

The invention relates to a device for recording vital signs, in particular for continuously determining the intra-arterial blood pressure on at least one finger of a hand, with the aid of a finger sensor. The device is based on the interaction between a base device and a body contact device coupled thereto via a special interface. The device preferably uses a plethysmographic arrangement with at least one light source, at least one light receiver or light detector, and at least one inflatable cuff.

The continuous, non-invasive measurement of blood pressure represents a major challenge for measurement technology to this day. The so-called Vascular Unloading Technique, which relates back to a publication by Penaz (Digest of the 10th International Conference on Medical and Biological Engineering, 1973, Dresden) and has been improved by various elements, is beginning to establish itself on the market.

In the Vascular Unloading Technique, near-infrared light is radiated into a finger, and the pulsatile (pulse-shaped) blood flow (actually the changing blood volume) in the finger is determined on the basis of the non-absorbed portion captured by a photodetector. For this process, also known as photoplethysmography (PPG), the (near-infrared) light is usually generated with the help of one or more light-emitting diodes (LED), which work with one or more wavelengths, and detected with the help of one or more light-sensitive receiver diodes (photodiodes). Instead of diodes, other types of photoreceivers are basically also suitable.

A control system then keeps the plethysmographically recorded flow (or the detected blood volume) and thus the resulting photoplethysmographic signal (volume signal $v(t)$) constant by applying counterpressure in a cuff (cuff pressure) $pc(t)$ on the finger. This counterpressure $pc(t)$ is usually regulated by a fast valve or valve system in conjunction with a pump. The related actuation of the valve or the valve system is carried out by a control unit, which is preferably implemented with a microcomputer. The main input signals in this case are the PPG signal $v(t)$ and the cuff pressure $pc(t)$. The pressure $pc(t)$ required to keep the PPG signal $v(t)$ constant then corresponds to the intra-arterial blood pressure $pa(t)$.

To do this, it is necessary that the cuff pressure $pc(t)$ is enabled to change at least as quickly as the intra-arterial blood pressure $pa(t)$ changes, so that the real-time condition is fulfilled. The upper limit frequency of $pa(t)$ and thus the highest rate of pressure change is greater than at least 20 Hz, which is definitely a challenge for a pressure control system. The result is that the pressure control by means of a valve or valve system is advantageously located in the immediate vicinity of the cuff. If the air lines are too long, there is a risk of losing this upper limit frequency condition due to the low-pass effect of the lines.

Numerous publications regarding the Vascular Unloading Technique are known:

A mechanical valve is known from U.S. Pat. No. 4,406,289 which regulates the counterpressure in the finger cuff with the desired accuracy when it is supplied with a linear pump. The valve is housed in a housing on the distal forearm and thus supplies the finger cuff with the pressure $pc(t)$ via a short tube.

U.S. Pat. No. 4,524,777 describes a pressure generation system for the Vascular Unloading Technique, a constant cuff pressure Pc also being generated with a linear pump, which is superimposed with pressure fluctuations $\Delta pc(t)$ from a shaker or a driving actuator connected in parallel.

U.S. Pat. No. 4,726,382 discloses a finger cuff for the Vascular Unloading Technique which has hose connections for the supply with the cuff pressure $pc(t)$. The length of the air tubes extends to the pressure generation system, which in turn is attached to the distal forearm.

WO 2000/059369 A1 also describes a pressure generation system for the Vascular Unloading Technique. The valve system here consists of a separate inlet valve and a separate outlet valve. While a relatively linear proportional pump must be used in U.S. Pat. Nos. 4,406,289 and 4,524,777, this system enables the use of simple, inexpensive pumps, since disruptive harmonics can be eliminated by the arrangement of the valves. Furthermore, the energy consumption of the simple pump can be significantly reduced by the valve principle.

WO 2004/086963 A1 discloses a system for the Vascular Unloading Technique in which the blood pressure can be continuously determined in one finger, while the measurement quality is checked in the neighboring finger (watchdog function). After a while, the system automatically replaces the measuring finger with the monitoring finger.

WO 2005/037097 A1 describes a control system for the Vascular Unloading Technique with several interlinked control loops.

WO 2010/050798 A1 discloses a pressure generation system (front end) attached to the distal forearm with only one valve, to which a finger cuff can be attached for the Vascular Unloading Technique.

With the pressure generation system described in WO 2011/045138 A1 for the Vascular Unloading Technique, the energy consumption of the pump is reduced similar to WO 2000/059369 and harmonics can be eliminated.

WO 2011/051819 A1 discloses an implementation of the Vascular Unloading Technique, improved by means of digital electronics, for increased stability and further miniaturization.

WO 2011/051822 A1 describes a method for the Vascular Unloading Technique, in which the measured signals $v(t)$ and $pc(t)$ are processed to increase long-term stability and to determine further hemodynamic parameters. In particular, a method for eliminating effects resulting from vasomotor changes in the finger arteries and a method for determining cardiac output (CO) are disclosed.

WO 2012/032413 A1 describes novel finger sensors that have a disposable part for single use. The cuff that comes into contact with the finger is housed in the disposable part for reasons of hygiene, whereas the associated pressure-generation and pressure-control system is housed in a reusable part. Accordingly, a separable pneumatic connection must be provided in this case between the disposable part and the reusable part.

As a rule, the pressure-generation and pressure-control system in the prior art is attached to the distal forearm, proximal to the wrist, which has significant disadvantages: This point is often used for intravenous access; also, the intra-arterial access at the distal end of the radial artery should be free for emergencies. Such accesses can be blocked by the pressure-generation and pressure-control system and its attachment. In addition, the system can slip or tilt during operation. This can have a detrimental effect on the fit of the sensors. The fit of the sensors would also be improved if the finger to be measured or the corresponding hand is in a certain resting position.

To overcome this problem, publication WO 2017/143366 A1 proposes a measuring system for the continuous determination of the intra-arterial blood pressure on at least one finger of a hand, with at least one finger sensor, with a plethysmographic system, with at least one light source, preferably LED, with one or more wavelengths, and at least one light sensor, and at least one inflatable cuff, as well as with a pressure-generation system with at least one valve regulated in real time with the aid of the plethysmographic system for generating a pressure in the cuff which essentially corresponds to the intra-arterial blood pressure in the finger, with the measuring system having a housing with a surface that serves as a support surface for the at least one finger and the adjacent areas of the palm. The hand rests here on a support under which there are essential components that were attached to the forearm in conventional systems.

Similar to previously mentioned WO 2012/032413 A1, the cuff is housed in a disposable part that can be separated from the housing (and thus from the hand support). Accordingly, a separable pneumatic connection must be provided in this case between the disposable part and the reusable part.

The pneumatic connection in the last-mentioned publications raises the problem that there are openings, in particular on the reusable housing, which may be difficult to clean and disinfect.

It is therefore the aim of the present invention to provide a device for the non-invasive recording of vital signs which enables improved cleaning and disinfection.

The aforementioned object is achieved according to the invention by means of a device for recording vital signs, in particular the arterial and/or venous blood pressure, according to claim 1. This device can also be referred to as a measuring system and preferably has at least one base device with means for applying pressure to a working fluid and a body contact device for the defined arrangement of a body part, in particular a finger or several fingers. The body contact device can be referred to as a finger sensor or finger positioning device or as an interchangeable part. The base device and the body contact device can be detachably coupled to one another to form an operating configuration, the base device having at least one housing for delimiting a receiving space, the housing having at least one contact surface for arranging the body contact device, the contact surface being closable by means of a closing member of a through-opening which can close the valve device, the valve device being arranged at least predominantly in the interior of the receiving space. The body contact device can thus be coupled to the housing and thereby to the base device. A spring, in particular made of metal or a polymer material, is preferably provided for applying spring force to the closing member. The working fluid is usually a gas, for example air, but reactions with a liquid as the working fluid are also advantageously possible. In the present application, fluid is generally understood to mean a gas or a liquid in accordance with the usual sense of the word. The spring can be a tension spring or a compression spring, the spring preferably being a helical spring. The closing member can be transferred by the spring into a position that closes the passage, and the passage is part of a fluid line on the base device side. In this case, the fluid line is preferably designed to conduct a gaseous working fluid, in particular air. The body contact device has at least one pressure applicator that can be acted upon by the working fluid, in particular for one or two fingers, for the controlled application of pressure to the body part, in particular in the case of several fingers, each of the fingers preferably individually. The body contact device preferably has at least one sealing element for creating a fluid connection to the base device. The sealing element preferably has one or at least one polymer material or consists of a polymer material. The sealing element preferably has a fixing part for arrangement at a receiving point of the body contact device and a sealing part. The fixing part and the sealing part are preferably connected to one another in one piece, with the fixing part and the sealing part possibly consisting of different materials (for example two or more component parts). The fixing part is preferably designed to enclose the receiving point and preferably extends in the longitudinal direction of the sealing element in a hollow or tubular form. The body contact device between the sealing element and the pressure applicator preferably has a fluid line on the body contact device side, wherein the sealing element can be pressed against the contact surface of the base unit in order to enclose the passage. The body contact device preferably has a pin-like, in particular protruding, deflecting means for deflecting the closing member. The deflecting means is preferably made of a polymer material or has a polymer material, but it can advantageously also be made of metal or metal-reinforced. In the operating configuration, the deflecting means deflects the closing member against the spring force and with the formation of the fluid connection.

This solution is advantageous because the body contact device and the base device are designed as separate devices and can thus fulfill different functions. The base device is preferably reusable, and the surface of the base device can be sterilized or disinfected. The body contact device can also be designed to be reusable. Alternatively, the body contact device can be intended for single use. The body contact device preferably does not have any electrical components required for the measurement or recording of vital signs.

Further preferred embodiments are the subject matter of the dependent claims and the following parts of the description.

According to a further preferred embodiment of the present invention, the closing member forms part of the contact surface of the housing, the part of the contact surface formed by the closing member being flush with the surrounding surface parts of the contact surface in a decoupled configuration (or non-operational configuration). This embodiment is advantageous because it enables simple and thorough cleaning of the surface of the base device. Flush here preferably means that the contact surface has no protrusions or recesses at the transition between the closing member and the housing.

Preferably, the surface portion of the contact surface has no hole or holes, recess(es), and/or groove(s) in a radius of up to 10 mm or up to 20 mm or up to 30 mm or up to 40 mm or up to 50 mm about the axial center of the closing member. This preferably applies to the entire contact surface or the entire surface of the base device. Preferably, the contact surface has an average roughness value of <5 µm or <1 µm or <0.5 µm or <0.1 µm or <0.05 µm or <0.01 µm.

According to a further preferred embodiment of the present invention, the sealing element has a conical or bell-shaped collar, the conical or bell-shaped collar enclosing the deflecting means at least temporarily and at least partially in the circumferential direction, the deflecting means being arranged in the center of the conical or bell-shaped collar, the conical or bell-shaped collar in the region of a first end being spaced further apart from the deflecting means in the radial direction than in the region of a second end, the first end of the conical or bell-shaped collar being intended for establishing contact with the contact surface. This embodiment is advantageous because the conical or bell-shaped collar supports easy attachment of the body contact device in the correct position on the base device.

Furthermore, there is advantageously a tolerance compensation in the axial and radial directions.

According to a further preferred embodiment of the present invention, the deflecting means is positioned fixedly opposite the sealing element, and at least or precisely one fluid passage is preferably formed between the conical or bell-shaped collar of the sealing element and the deflecting means, preferably several fluid passages are formed. The fluid passage or the fluid passages are preferably to be understood as axial holes or bores.

According to a further preferred embodiment of the present invention, the deflecting means is movably arranged with respect to the sealing element, the sealing element forming a passage, the passage being fluid-tightly closable by the deflecting means, the deflecting means closing the passage of the sealing element in a non-use configuration and enabling it in the operating configuration. This embodiment is advantageous because the risk of contamination of the working fluid line components formed in the body contact device and/or the working fluid absorption components by biological material such as bacteria, viruses, or fungi is reduced or limited. A seal against the penetration of cleaning agents or disinfectants can also advantageously be achieved in this way.

According to a further preferred embodiment of the present invention, a spring is provided for deflecting the deflecting means, the deflecting means preferably being deflectable in a straight line, the spring being more compressed in the operating configuration than in the non-use configuration as a result of the straight deflection of the deflecting means. This embodiment is advantageous because the fluid connection between the body contact device and the base device is generated automatically and only when the two devices are mechanically coupled to one another.

According to a further preferred embodiment of the present invention, the deflection of the deflecting means or the deflecting element is limited by a stop, wherein the passage can be moved, according to the amount, closer to the base device than the deflecting element can be deflected or than the closing member of the valve device of the base device is deflected or is deflectable, as a result of the deformation of the conical or bell-shaped collar. The spring force of the spring acting on the closing member is preferably different from the spring force of the spring acting on the deflection element. It is preferably higher or lower. Alternatively, the spring forces can also be the same. This embodiment is advantageous since the creation of the fluid connection causes the individual line sections to be released at different times when the spring forces are different. According to a further preferred embodiment of the present invention, the deflection of the deflection element and the deflection of the closing member of the valve device of the base device correspond in total to the approach of the passage of the sealing element to the contact surface resulting from the deformation of the conical collar.

According to a further preferred embodiment of the present invention, at least one pump device for pressurizing the working fluid, in particular air, is provided on the base device side, the pump device preferably being coupled directly to the fluid line. Alternatively, it is possible to provide an external pump device that can be connected to the base device.

At least one optical signal source and one optical sensor device are preferably provided as part of the housing or within the housing, with the pump device or the pressure applicator or a valve device being provided in the fluid line, in particular in a manner which it can be controlled or actuated as a function of optical signals which the optical sensor device detected. The pressure applicator can have a valve device which can be actuated or controlled, or a valve device which can be actuated or controlled can be part of the fluid line or the pump device. The valve device or pressure-setting valve device in this case can be actuatable for setting a constant pressure or a predetermined or predeterminable pressure curve. In particular, the valve device or pressure-setting valve device can be actuated electrically. The valve device or pressure-setting valve device is preferably arranged in the base device or in the body contact device.

The above-mentioned object is also achieved by means of a base device for use in a device according to the invention described herein. The base device preferably has at least one housing for delimiting a receiving space, the housing having at least one contact surface for arranging the body contact device, the contact surface having a passage that can be closed by means of a closing member of a valve device, the valve device being arranged at least for the most part in the interior of the receiving space, a spring being provided for applying spring force to the closing member, the closing member being transferable by the spring into a position that closes the passage, and the passage opening being part of a fluid line on the base unit, with at least one pump device for pressurizing the working fluid, in particular air, being provided, with the pump device being coupled to the fluid line.

According to a preferred embodiment of the present invention, at least one optical signal source is provided as part of the housing of the base device or within the housing of the base device and/or at least one optical sensor is provided as part of the housing of the base device or within the housing of the base device. The pump device is preferably controlled as a function of signals or data from the sensor device or can be controlled as a function of signals or data from the sensor device, it being possible to generate the signals or data from the sensor device as a function of detected optical signals, which result from optical signals which are emitted by the optical signal source. It is also possible for a processor device or control device to be part of the base device. The processor device or control device preferably takes on the processing and/or evaluation of the sensor data and/or possible valve controls and/or the pump control. This solution is advantageous because all or at least most of the actuators or active devices, elements, and/or components are preferably part of a compact unit.

The above-mentioned object is also achieved by a body contact device for use in a device according to the invention. The body contact device preferably has at least one pressure applicator, in particular a cuff, that can be acted upon with a working fluid, in particular air, for the controlled application of pressure to a body part, in particular one or more fingers, and the pressure applicator preferably specifies a positioning of the body part on the body contact device. At least one sealing element is preferably provided for releasably coupling the body contact device to a working fluid supply device, in particular a base device according to claim 10, the body contact device preferably having a fluid line extending between the sealing element and the pressure applicator, the body contact device particularly preferably having a pin-shaped deflecting means, wherein the pin-shaped deflecting means is completely enclosed by the sealing element along its longitudinal extension direction, at least in sections or at least temporarily. This solution is advantageous because the position of the hand or the finger or fingers is directly predetermined. Furthermore, the body contact device can be designed very inexpensively and is therefore suitable for inexpensive single use.

At least one light guide for delivering radiation to the body part and/or for providing radiation to a sensor device is provided according to a further preferred embodiment of the present invention, with the fluid stream flowing through the fluid line, in particular the pressure of the fluid stream, being controllable as a function of the radiation conducted through the light guide. This embodiment is advantageous because the body part to be examined is not placed on the base device, but on the body contact device arranged thereon. Thus, there is little or no contact between the base device and the body part, as a result of which contamination of the base device is limited.

The above devices can, in particular, be used for continuous, non-invasive measurement of arterial blood pressure. The method preferably comprises the following steps: providing a device according to any of claims 1 to 9, wherein the base device and the body contact device are coupled to one another in an operating configuration; positioning a body part, in particular a finger or several fingers, in the pressure applicator; generating an optical signal by means of an optical signal source, with the signal source being part of the base device or the body contact device, with the optical signal being coupled into the body part; detecting of the optical signal after coupling into the body part, in particular after scattering and/or reflection by the body part, by means of an optical sensor device, with the optical sensor device being part of the base device or the body contact device; generating a signal or data by the optical sensor device, the signal or data representing the detected optical signal; setting a pressure exerted by means of the pressure applicator to the body part as a function of the signal generated by the optical sensor device or the data generated.

According to a further preferred embodiment of the present invention, the signal source, the sensor device, and the pump device are part of the base device, wherein the optical signal generated by the signal source is passed from the base device through the body contact device to the body part, and wherein the radiation scattered and/or reflected by the body part is passed through the body contact device to the base device, and wherein the working fluid conveyed by the pump device is air, with the air being conveyed from the base device into and through the fluid line in the body contact device to the pressure applicator. A measurement according to the Vascular Unloading Technique is made possible by the interaction of the sensor device, the signal source, and the pressure generation/pressure setting in the pressure applicator, in particular the cuff, in particular by means of the pump device and/or a controlled valve device.

Further advantages, objectives, and properties of the present invention are explained with reference to the following description of the attached drawings, in which the device according to the invention or components of the device according to the invention are shown by way of example. Components or elements that are preferably used in the device according to the invention or the method according to the invention and/or which correspond at least essentially with regard to their function in the figures can be identified with the same reference numerals, wherein these components or elements do not have to be numbered or explained or implemented in all figures.

The following is shown:

FIG. 1a-d a schematic example of a device according to the invention, the components thereof (base device and body contact device), and the arrangement of a body part on the device schematically;

FIG. 2a a line section of a body contact device with a sealing element fixedly arranged thereto and fixedly arranged deflecting means;

FIG. 2b a line section of a body contact device, in which a sealing element is disposed on the line section, and a movably arranged deflecting means interacts with the sealing element in a sealing manner. The sealing element thus forms two effective sealing surfaces spaced apart from one another, one effective sealing surface being designed to interact with the deflecting means and one effective sealing surface being designed to interact with a contact surface of a base device.

FIG. 3a a first valve device, said valve device being at least partially disposed directly in a valve housing, in which the valve housing is arranged or formed in the housing of the base device;

FIG. 3b a second valve device, said valve device being at least partially disposed or formed in the base device;

FIG. 4a the arrangement shown in FIG. 2b in conjunction with arrangement shown in FIG. 3b in a first state in which the seal, in particular the collar is deformed; and FIG. 4b the arrangement shown in FIG. 2b in conjunction with the arrangement shown in FIG. 3b in a second state in which the seal, in particular the collar, and the springs have deformed, whereby a fluid line is opened or released or formed between the base device and the body contact device;

FIG. 5a the arrangement shown in FIG. 2a in conjunction with the arrangement shown in FIG. 3b in a first state, i.e. in a decoupled state; and FIG. 5b the components shown in FIG. 5a in a second state, in which, in this second state, the seal, in particular the collar, is deformed, and the deflecting means deflects the closing member against the spring force; and FIG. 6 the arrangement shown in FIG. 5a schematically in a perspective illustration and in a perspective sectional illustration.

FIG. 1a shows an example of a body contact device 2 according to the invention. This body contact device 2 has a pressure applicator 18, in particular a cuff or pressure cuff. In an operating state, the pressure applicator is in functional, in particular fluidic, connection via one or more fluid lines with a pump device 1 arranged in a base device 1 (cf. FIG. 1b). The reference numeral 30 designates, purely schematically, a light coupling surface for coupling or decoupling light from or into a light guide for providing radiation to a body part 4 (cf. FIG. 1d) and/or for supplying light that was reflected and/or scattered from the body part to a sensor device. Alternatively, the device can also be designed in such a way that a light source or a light detector for the direct coupling or decoupling of light from or into the body part is provided in the body contact device 2 or base device 1 without an interposed light guide.

Reference numeral 20 denotes a sealing element or seal or sealing device, which preferably has a bell-shaped or (as shown) conical collar 24.

The sealing element 20 can be arranged around a closing member 10 of a valve device 12 (cf. FIGS. 3a and 3b) on a surface 8 of the base device 1.

FIG. 1c shows a schematic representation of the device 3 according to the invention.

In FIG. 1d, the device 3 according to the invention is shown schematically with a human hand 4 arranged thereon.

FIG. 2a shows a fluid line element of the body contact device 2, which is surrounded at least in sections by the sealing element 20. The sealing element 20 has at least or precisely one passage 26. The passage(s) 26 is/are preferably always open or unlocked. The reference numeral 22 in this case denotes a deflecting means for repositioning the closing member 10.

FIG. 2b shows an alternative fluid line element of the body contact device 1, it being possible for the deflecting means 22 to be pressed against a preferably central passage of the sealing element 20 via a spring 28 with a sealing surface 23. The sealing element 20 also has a conical collar 24. In this case, the sealing element 20 preferably has precisely one passage.

FIG. 3a shows a first valve device 12. The valve device 12 has a closing member 10 which is flush with the surface 8 of the base device 1 or the housing 6 of the base device. The reference numeral 32 denotes a compressed air supply, in particular starting from a pump device.

FIG. 3b shows a second valve device 12. According to this valve device 12, a valve housing 13 is provided, by means of which the valve device 12 is coupled to the housing 6 of the base device 1.

FIG. 4a shows the valve device from FIG. 3b and the arrangement from FIG. 2b in a first state. The sealing element 20 already has a first deformation and the deflecting means 22 already effects a repositioning of the closing member 10. However, the sealing surface 23 still seals in this state.

In FIG. 4b, the deformation of the sealing element 20, in particular of the collar 24, has progressed further, as a result of which the line element of the body contact device 2 has moved closer to the base device 1. After a defined deflection of the closing member 10, there is then a relative movement of the sealing element 20 with respect to the deflecting means 22, whereby the passage 26 is released.

FIG. 5a shows the arrangement from FIG. 2 and the valve device 12 from FIG. 3b. In this case, the sealing element 20 can only experience a deformation, and the closing member 10 can be deflected. The deflection of the closing member 10 is preferably directly related to a deformation of the sealing element 20. This relationship is shown by FIG. 5b.

In FIG. 6, the arrangement shown in FIG. 5a is shown in a perspective illustration and in a sectional illustration.

The present exemplary embodiment thus relates to a device 3 for recording vital signs. This device 3 has: a base device with a pump device for pressurizing a working fluid and a body contact device 2 for the defined arrangement of a body part 4, in particular a finger, the base device 1 and the body contact device 2 being releasably coupled to one another to form an operating configuration, in which the base device 1 has a housing 6 for delimiting a receiving space, the housing 6 has a contact surface 8 for the arrangement of the body contact device 2, the contact surface 8 has a passage 14 that can be closed by means of a closing member 10 of a valve device 12, the valve device 12 is arranged, at least predominantly, in the interior of the receiving space, in which a spring 16 is provided for spring force loading of the closing member 10, in which the closing member 10 is transferred by the spring 16 into a position closing the passage 14, and in which the passage 14 is part of a fluid line on the base device, in which the body contact device 2 has at least one pressure applicator 18, which can be acted upon by the working fluid, for the controlled application of pressure to the body part 4, in which the body contact device 2 has at least one sealing element 20 for creating a fluid connection with the base device 1, in which the body contact device 2 has a fluid line on the body contact device side between the sealing element 20 and the pressure applicator 18, in which the sealing element 20 can be pressed against the contact surface 8 to enclose the passage 14, in which the body contact device 2 has a deflecting means 22 for deflecting the closing member 10, in which the deflecting means 22, in the operating configuration, deflects the closing member 10 against the spring force and with the formation of the fluid connection.

LIST OF REFERENCE NUMERALS

1 Base device
2 Body contact device
3 Device
4 Body part (first body part/first finger)
5 Second body part (second finger)
6 Housing
8 Contact surface
10 Closing member
12 Valve device
13 Valve housing
14 Passage
16 Spring
18 Pressure applicator/cuff
20 Sealing element
22 Deflecting means
23 Sealing surface between seal and deflecting means
24 Collar
26 Fluid passage/passage (in the sealing element)
28 Spring (for deflecting the deflecting means)
30 Light coupling surface
32 Compressed air supply
34 Fluid line in the body contact device

The invention claimed is:

1. A device for recording vital signs, comprising:
a base device comprising means for controlled pressurization of a working fluid; and
a body contact device for defined positioning of a body part,
wherein the base device and the body contact device are releasably coupled to each other to form an operating configuration,
wherein the base device comprises a housing for delimiting a receiving space, the housing comprising a contact surface for receiving said body contact device,
wherein the contact surface comprises a passage that is closable by a closing member of a valve device,
wherein the valve device is arranged at least predominantly in an interior of the receiving space,
wherein a spring is provided for spring-loading the closing member,
wherein the closing member is moveable by the spring into a position closing the passage, and
wherein the passage is a component of a first fluid line on a side of the base device,
wherein the body contact device comprises a pressure applicator, that is configured to be acted upon by the working fluid for controlled pressurization of the body part,
wherein the body contact device comprises at least one sealing element configured for establishing a fluid connection to the base device,
wherein the body contact device comprises a second fluid line on a side of the body contact device between the sealing element and the pressure applicator,
wherein the sealing element is pressable against the contact surface for enclosing the passage,
wherein the body contact device comprises a deflecting means for deflecting the closing member, and wherein the deflecting means, in the operating configuration, deflects the closing member against the spring force with formation of the fluid connection.

2. The device according to claim 1, wherein the closing member forms a part of the contact surface of the housing, wherein the part of the contact surface formed by the closing member terminates flush with surrounding surface parts of the contact surface in a decoupled configuration.

3. The device according to claim 1, wherein the sealing element comprises a conical or bell-shaped collar, wherein the conical or bell-shaped collar encloses the deflecting means at least temporarily and at least in sections in a circumferential direction, wherein the deflecting means is arranged in the center of the conical or bell-shaped collar,
wherein the conical or bell-shaped collar is at a greater distance in a radial direction from the deflecting means in an area of a first end of the conical or bell-shaped collar than in an area of a second end of the conical or bell-shaped collar, wherein the first end is configured for establishing contact with the contact surface.

4. The device according to claim 3, wherein the deflecting means is fixedly positioned in relation to the sealing element, and at least one fluid passage is formed between the conical or bell-shaped collar of the sealing element and the deflecting means.

5. The device according to claim 1, wherein the deflecting means is movably arranged with respect to the sealing element, wherein the sealing element forms a passage that is closable in a fluid-tight manner by the deflecting means, wherein the deflecting means closes the passage of the sealing element in a non-use configuration and opens the passage of the sealing element in the operating configuration.

6. The device according to claim 5, comprising:
a spring for deflecting the deflecting means, wherein the deflecting means is deflectable in a straight line, wherein the spring for deflecting the deflecting means is more strongly deflected, in the operating configuration as a result of a straight deflection of the deflecting means than in the non-use configuration.

7. The device according to claim 6, wherein the deflection of the deflecting means is limited by a stop, wherein the passage of the sealing element can be moved closer to the base device more by deforming a conical or bell-shaped collar of the sealing element than by the deflecting means or by the closing member of the valve device of the base device being deflected.

8. The device according to claim 7, wherein the deflection of the deflecting means and the deflection of the closing member in total correspond to an approach of the passage of the sealing element toward the contact surface due to the deformation of the conical or bell-shaped collar.

9. The device according to claim 1, comprising:
a pump device that is part of the means for controlled pressurization of the working fluid, on the side of the base device, wherein the pump device is coupled to the first fluid line;
at least one optical signal source for transmitting optical signals into tissue of the body part; and
an optical sensor device for detecting the optical signals after passing through, or being reflected by, the tissue of the body part,
wherein at least one functional parameter of at least one of the pump device or of the pressure applicator is configured to be regulated as a function of the detected optical signals.

10. The device according to claim 1, wherein a pump device is part of the means for controlled pressurization of the working fluid, is provided, wherein the pump device is coupled to the first fluid line.

11. The device according to claim 10, further comprising at least one of:
at least one optical signal source for emitting optical signals in the tissue of the body part, wherein the at least one optical signal source is part of the housing of the base device or within the housing of the base device, or
at least one optical sensor for detecting resulting optical signals from the tissue of the body part, wherein the at least one optical sensor is part of the housing of the base device or within the housing of the base device,
wherein at least one functional parameter of at least one of the pump device or of the pressure applicator is configured to be regulated as a function of the resulting optical signals detected.

12. The device according to claim 1, wherein the pressure applicator specifies the body part to be positioned on the body contact device,
wherein the sealing element is provided for releasably coupling the body contact device to a working fluid supply device,
wherein the deflecting means is pin-shaped, wherein the pin-shaped deflecting means is at least temporarily enclosed by the sealing element along its longitudinal extension direction.

13. The device according to claim 12, further comprising:
at least one light guide configured for at least one of (i) supplying radiation to the body part or (ii) for providing radiation to a sensor device.

* * * * *